United States Patent
Li et al.

(10) Patent No.: US 12,042,277 B2
(45) Date of Patent: Jul. 23, 2024

(54) BLOOD TESTING METHOD AND APPARATUS

(71) Applicant: SHENZHEN MINDRAY BIO-MEDICAL ELECTRONICS CO., LTD., Shenzhen (CN)

(72) Inventors: Xuerong Li, Shenzhen (CN); Huilin Shi, Shenzhen (CN); Jianchao Liu, Shenzhen (CN); Bo Ye, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 198 days.

(21) Appl. No.: 16/729,161

(22) Filed: Dec. 27, 2019

(65) Prior Publication Data
US 2020/0129100 A1 Apr. 30, 2020

Related U.S. Application Data

(63) Continuation of application No. PCT/CN2017/090816, filed on Jun. 29, 2017.

(51) Int. Cl.
A61B 5/145 (2006.01)
G01N 15/01 (2024.01)
(Continued)

(52) U.S. Cl.
CPC ..... *A61B 5/14535* (2013.01); *G01N 15/1404* (2013.01); *G01N 21/64* (2013.01);
(Continued)

(58) Field of Classification Search
CPC ........... A61B 5/14535; G01N 15/1404; G01N 21/64; G01N 2015/0073; G01N 2015/0084; G01N 2015/1486
See application file for complete search history.

(56) References Cited

U.S. PATENT DOCUMENTS 5,656,499 A  *  8/1997  Chupp .................. G01N 15/14
                                                        436/805
6,525,807 B1     2/2003  Morikawa et al.

FOREIGN PATENT DOCUMENTS

| CN | 101236194 A | 8/2008 |
| CN | 101358960 A | 2/2009 |

(Continued)

OTHER PUBLICATIONS

Baumgarten, Andrea, et al. "Measurement of platelet aggregation in ovine blood using a new impedance aggregometer." Veterinary Clinical Pathology 39.2 (2010): 149-156. (Year: 2010).*

(Continued)

*Primary Examiner* — Robert J Eom
(74) *Attorney, Agent, or Firm* — Kory D. Christensen

(57) ABSTRACT

A blood detection method and a blood detection device are disclosed. When a count number of platelet in a blood sample is less than a predetermined value, a detection solution of the blood sample is prepared. A cell statistical amount of the detection solution of the blood sample is increased to obtain the platelet detection result. The cell statistics amount of the detection solution of the blood sample may be increased in an impedance detection area to perform PLT-I detection, or in an RET detection area; or performing both of RET detection and PLT-O detection simultaneously. Thus, the accuracy of platelet detection can be improved when the number of platelets in the blood sample is low.

7 Claims, 6 Drawing Sheets

(51) Int. Cl.
*G01N 15/14* (2024.01)
*G01N 15/1404* (2024.01)
*G01N 21/64* (2006.01)

(52) U.S. Cl.
CPC ............... *G01N 2015/012* (2024.01); *G01N 2015/018* (2024.01); *G01N 2015/1486* (2013.01)

(56) References Cited

FOREIGN PATENT DOCUMENTS

| CN | 102539300 A | 7/2012 |
|----|-------------|--------|
| CN | 103941026 A | 7/2014 |
| CN | 104297133 A | 1/2015 |
| CN | 106872379 A | 6/2017 |

OTHER PUBLICATIONS

Segal, H. C., et al. "Accuracy of platelet counting haematology analysers in severe thrombocytopenia and potential impact on platelet transfusion." British journal of haematology 128.4 (2005): 520-525. (Year: 2005).*

Würtz, Morten, et al. "Platelet aggregation is dependent on platelet count in patients with coronary artery disease." Thrombosis research 129.1 (2012): 56-61. (Year: 2012).*

Boulassel, Mohamed-Rachid, et al. "Accuracy of platelet counting by optical and impedance methods in patients with thrombocytopaenia and microcytosis." Sultan Qaboos University Medical Journal 15.4 (2015): e463. (Year: 2015).*

* cited by examiner

BLOOD TESTING METHOD AND APPARATUS

CROSS-REFERENCE TO RELATED APPLICATIONS

This application is a continuation of Patent Cooperation Treaty Application No. PCT/CN2017/090816, filed on Jun. 29, 2017, the content thereof is hereby incorporated by reference in its entirety.

TECHNICAL FIELD

The present disclosure relates to the field of testing, in particular to a blood testing method and apparatus.

BACKGROUND

In a routine blood test, platelet detection is often completed through an impedance channel, which is referred to as PLT-I detection. That is, the PUN detection is performed by passing a test solution prepared from a blood sample through the impedance channel to obtain a PLT (blood platelet) detection result.

As the platelet detection result is of great importance as a reference in clinical applications, the requirement for the accuracy of platelet detection is harsh. In PLT-I detection, in the case of a sample with a low platelet count, it may fail to obtain an accurate detection result as the number of platelets counted is small.

Therefore, it is necessary to develop a method that can accurately detect platelets, especially of a low platelet count.

SUMMARY

An embodiment provides a blood testing method and apparatus for improving testing accuracy of a low platelet count.

A first aspect of the embodiment provides a blood testing method, including preparing a first test solution by using a blood sample, and then, controlling the first test solution to pass through an impedance detection area, thereby performing platelet detection on the first test solution by using an impedance method in the impedance detection area to obtain a first platelet detection result. A second test solution is prepared by using the blood sample or the second test solution is drawn from the remaining test solution of the first test solution when the first platelet detection result is less than a preset platelet detection threshold. Then, the second test solution is controlled to pass through the impedance detection area, thereby performing platelet detection on the second test solution by using an impedance method in the impedance detection area to obtain a second platelet detection result, wherein a statistical amount of the second test solution passing through the impedance detection area is greater than a statistical amount of the first test solution passing through the impedance detection area.

In this way, when a low platelet count of a sample is detected by the impedance method, the platelet detection is re-conducted using the test solution of the blood sample, and the platelet are detected again by the impedance method in the impedance detection area with an increased statistical amount of the test solution, thereby obtaining a second platelet detection result. By the PLT-I detection with an increased statistical amount, the detection accuracy of PLT-I can be improved, i.e. the second platelet detection result is more accurate. The method of the embodiment is particularly useful for instruments equipped without or not switching on an optical RET or optical PLT channel. Being independent of fluorescence detection, the instruments have reduced manufacturing costs and usage costs while maintaining high detection accuracy.

A second aspect of the embodiment provides a blood testing method, including preparing a second test solution by using the blood sample when low platelet count information of the blood sample is obtained, wherein the low platelet count information indicates that a platelet content of the blood sample is less than a preset platelet detection threshold. Then, the second test solution is controlled to pass through an RET detection area, thereby performing optical detection on the second test solution in the RET detection area to obtain an RET detection result and a second platelet detection result, wherein the statistical amount of the second test solution passing through the RET detection area is greater than a preset statistical amount.

The method of the embodiment is suitable for instruments equipped with and switching on an optical RET channel. When a blood sample is a low platelet count sample, platelet detection and RET detection are simultaneously carried out on the blood sample via an optical detection method in the RET detection area with an increased statistical amount, which improves the accuracy of platelet detection as well as the detection efficiency, since the RET detection and PLT-O detection are completed at once to obtain the RET detection result and PLT detection result simultaneously, thus reducing the consumption of samples and reagents and saving the costs.

A third aspect of the embodiment provides a blood testing apparatus that includes a preparation unit configured for preparing a first test solution by using a blood sample, a controller configured for controlling the first test solution to pass through an impedance detection area, and a detection unit configured for detecting platelets of the first test solution by using an impedance method in the impedance detection area to obtain a first platelet detection result. The preparation unit is further configured for preparing a second test solution by using the blood sample or by aspirating the remaining test solution of the first test solution when the first platelet detection result is less than a preset platelet detection threshold. The controller is further configured for controlling the second test solution to pass through the impedance detection area. The detection unit is further configured for detecting platelets of the second test solution by using an impedance method in the impedance detection area to obtain a second platelet detection result. A statistical amount of the second test solution passing through the impedance detection area is greater than a statistical amount of the first test solution passing through the impedance detection area.

A fourth aspect of the embodiment provides a blood testing apparatus that includes a preparation unit configured for preparing a second test solution by using the blood sample when low platelet count information of the blood sample is obtained, a controller configured for controlling the second test solution to pass through an RET detection area, and a detection unit configured for performing an optical detection on the second test solution in the RET detection area to obtain an RET detection result and a second platelet detection result. The low platelet count information indicates that a platelet content of the blood sample is less than a preset platelet detection threshold. The statistical amount of the second test solution passing through the RET detection area is greater than a preset statistical amount.

A fifth aspect of the embodiment provides a computer-readable storage medium, having instructions stored therein which, when executed on a computer, cause the computer to perform the methods described in the first and second aspects.

A sixth aspect of the embodiment provides a computer program product comprising instructions which, when executed on a computer, cause the computer to perform the methods described in the first and second aspects.

In the technical solution provided by the embodiment, when low platelet count information of a blood sample is acquired, the blood testing method of the embodiment uses the blood sample to prepare a test solution, and increases the statistical amount of the test solution of the blood sample passing through a detection area to obtain a platelet detection result. The way to increase the statistical amount of the test solution of the blood sample can be increasing the statistical amount in the impedance detection area for PLT-I detection; or increasing the statistical amount in the RET detection area and performing RET detection and PLT-O detection together. In this way, when the number of platelets in the blood sample is low, the accuracy of detection in the case of a low platelet count can be improved.

DETAILED DESCRIPTION OF EMBODIMENTS

The terms "first", "second", "third", "fourth", etc. (if any) in the specification and the claims and the above-mentioned drawings are used to distinguish similar objects and are not necessarily used to describe a specific order or sequence. It should be understood that the terms used as such is interchangeable where appropriate, so that the embodiments described herein can be implemented in an order other than what is illustrated or described herein. In addition, the terms "comprise", "include" and "have" and any variations thereof are intended to cover non-exclusive inclusion. For example, a process, method, system, product, or apparatus that comprises a series of steps or units is not necessarily limited to those steps or units explicitly listed, but may include other steps or units not explicitly listed or inherent to such a process, method, product, or apparatus.

Figure 1:
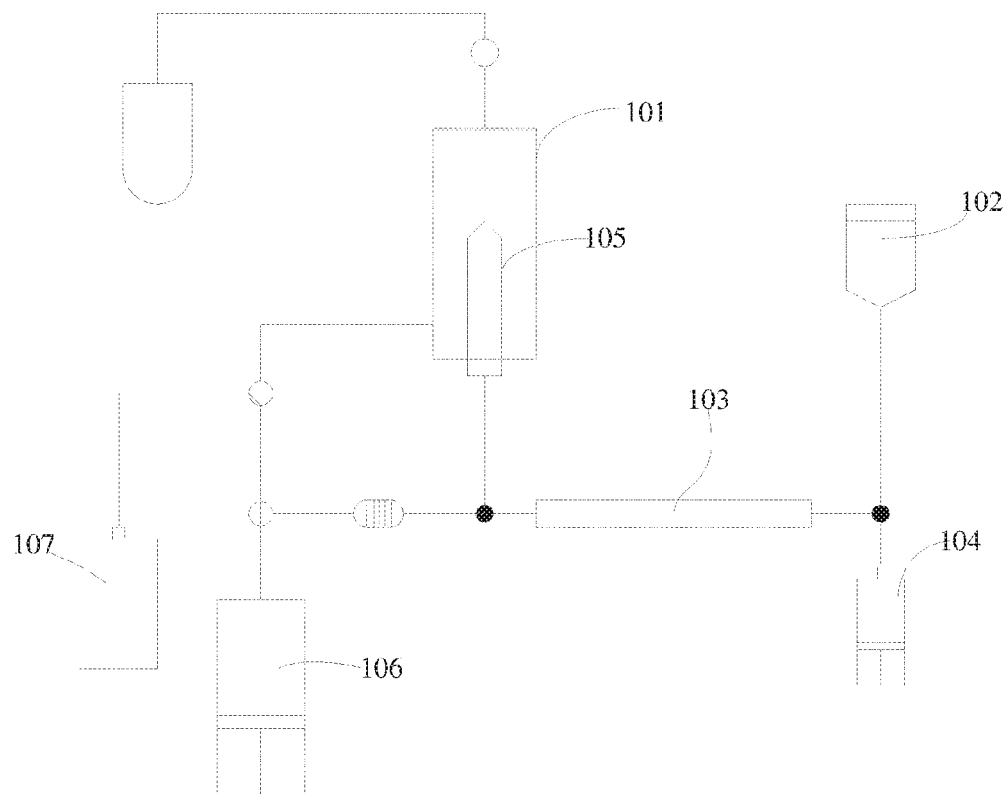
FIG. 1 is a schematic structure diagram of a blood testing apparatus provided by an embodiment of the present disclosure.

FIG. 1 is a schematic structure diagram of a blood testing apparatus provided by an embodiment of the present disclosure. As shown in FIG. 1, the blood testing apparatus comprises a counting tank 101, a reaction tank 102, a sample preparation tube 103, a sample injector 104, a sample needle 105, a sheath fluid injector 106, and a diluent barrel 107. The reaction tank 102 is configured for storing the test solution to be tested. In some embodiments, the blood testing apparatus draws blood samples and reagents into the reaction tank 102, and in the reaction tank 102, the blood samples and reagents react to obtain the test solution to be tested. In the process of platelet detection, the blood testing apparatus controls the test solution to be tested in the reaction tank 102 to flow to the sample preparation tube 103. Then, the sample injector 104 pushes the test solution stored in the sample preparation tube 103 into the counting tank 101, and the sample needle 105 causes the test solution to be injected into the counting tank 101 therethrough. The diluent barrel 107 is configured for storing a sheath fluid, and the sheath fluid injector 106 is configured for providing drive for the sheath fluid in the diluent barrel to flow to the counting tank 101. Under the cooperation of the sheath fluid injector 106 and the sample injector 104, the sheath fluid and the test solution respectively flow to the counting tank 101. In the counting tank 101, the test solution wrapped by the sheath fluid passes through a detection area of the counting tank 101 for detection of a platelet content.

The detection area of the counting tank 101 may be a detection area for detecting platelets using an impedance method, that is, a PLT-I (blood platelet-impedance) detection area. The detection principle is the electrical impedance principle, namely the Coulter principle: blood cells are relatively poor conductors of electricity, so that when they are suspended in an electrolyte solution and passing through a detection micro-orifice, the original constant resistance inside and outside the micro-orifice will be changed, resulting in electric pulses. The amplitude of pulses represents the volume of the blood cells passing through the micro-orifice, and the number of pulses represents the number of the blood cells passing through the micro-orifice. The electrical pulse signal, i.e. impedance signal, can be acquired and analysed by a blood testing apparatus to detect the platelet content. Platelet detection using the electrical impedance principle is platelet detection using an impedance method, which can be referred to as detection.

Figure 2:
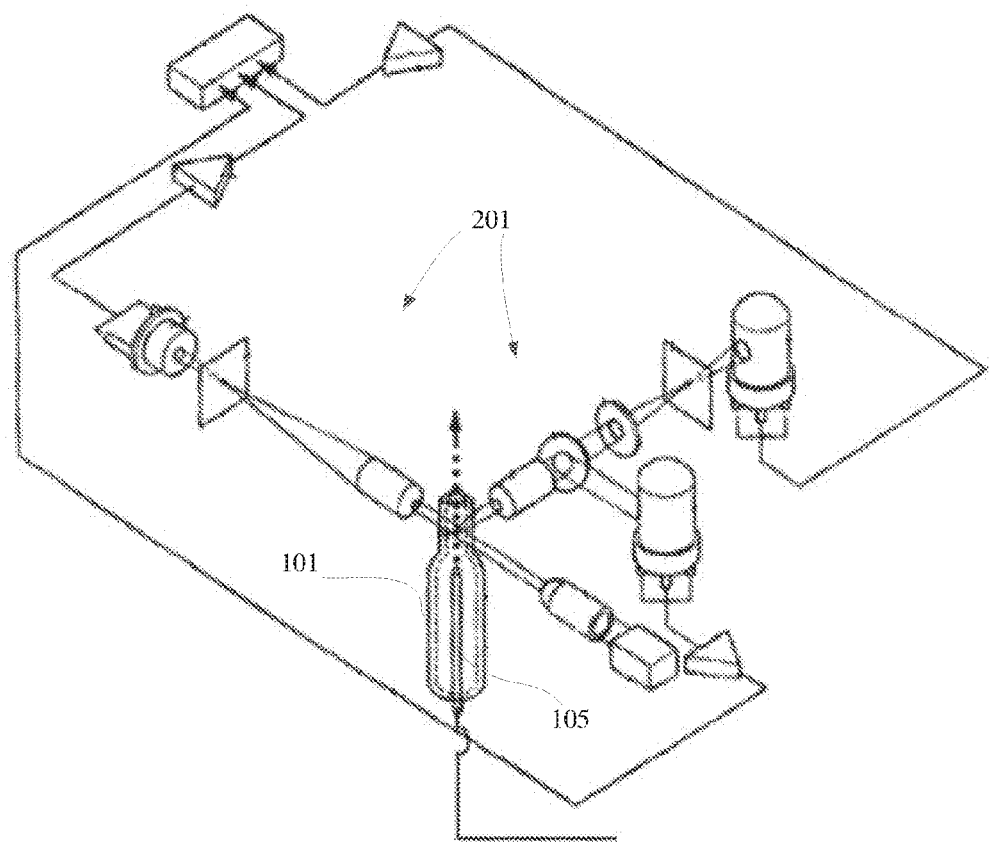
FIG. 2 is a schematic structure diagram of a blood testing apparatus provided by another embodiment of the present disclosure.

In some embodiments, as shown in FIG. 2, the detection area of the counting tank may also be a detection area for detecting platelets by a fluorescence method, such as an RET (Reticulocyte) detection area. In the RET detection area, RET parameters of the test solution can be detected. The platelet detection of the test solution can also be performed using a fluorescence method. Platelet detection using the fluorescence method can be referred to as PLT-O (blood platelet-optical) detection. The principle of PLT-O detection is an optical principle: the sheath flow fluid formed by the accumulation of individual blood to cells with hydrodynamic force refracts, diffracts and scatters the light beam when passing through the detection area irradiated by a laser (monochromatic light generated by excitation of inert substances such as helium and neon), and a light scattering detector generates pulses after receiving the light beam, wherein the amplitude of the pulses is proportional to the size of the irradiated cells, and the number of pulses represents the number of the irradiated cells. In this case, the blood testing apparatus is also provided with an optical detection apparatus 201. RNA (ribonucleic acid) of platelets binds with fluorescent dye in the reaction tank. Therefore, when the platelets pass through the RET detection area of the counting tank 101, under the light irradiation of the optical detection apparatus 201, various optical signals generated by the platelets due to the light irradiation are collected by the optical detection apparatus and converted into corresponding electrical signals. The information carried by these optical signals and the corresponding electrical signals thereof corresponds to the characteristics of platelet particles and can be used as the characteristic data of cell particles. The detection of platelets can be achieved by analyzing these optical signals and the corresponding electrical signals thereof.

It can be understood that the above blood testing apparatus shown in FIGS. 1 and 2 is only one of the apparatus provided by the present disclosure, and the blood testing apparatus shown in FIG. 1 is not a limitation to the blood testing method and apparatus of the embodiment of the present disclosure. For example, while FIG. 1 shows a single reaction tank, in fact, the blood testing apparatus can have a plurality of different reaction tanks, and test solutions for detecting different blood cells can be prepared in different reaction tanks.

The blood testing apparatus of some embodiments of the present disclosure and the blood testing apparatus that performs the blood testing method of the embodiments of the present disclosure may comprise the following structural features: the sample test solution for measurement can be continuously supplied, for example, the sample injector shown in FIG. 1 can push multiple statistical doses of test solution into the counting tank; and the measurement environment can be continuously provided, for example, the provision of sheath fluid can meet the requirement of multiple statistical doses of test solution. Moreover, the blood testing apparatus provided by some embodiments of the present disclosure can decide and implement the measurement time or the control of corresponding statistical amount for corresponding platelet detection.

According to the blood testing method of some embodiments of the present disclosure, in the case of the amount of the blood sample available being greater than the amount of the sample actually configured for testing, when a low platelet count sample is encountered, measurement can be performed by using the sample fluid which has not been configured for measurement, so that a larger statistical amount of sample can be obtained.

The embodiment of the present disclosure provides two blood testing methods, which are respectively shown in Scenario I and Scenario II below. When acquiring low platelet count information of a blood sample, the two blood testing methods both increase the statistical amount of a test solution of the blood sample so as to improve the accuracy of the low platelet count when the number of platelets is small. The method provided by Scenario I is to increase statistical amount in the impedance detection area for performing the PLT-I detection; and the method provided in Scenario II is to increase statistical amount in the RET detection area for performing the RET detection and PLT-O detection. Both methods can include such a technical solution: after measurement for the first test solution is finished, the user obtains the first platelet detection result, and the blood testing apparatus can determine the retest triggering condition, so that driven by the retest triggering condition, the blood testing apparatus can draw the sample anew to perform platelet detection. Optionally, the retest triggering conditions can be determined by the user, for example, retest can be configured to be triggered when PLT is less than 50, or to be triggered when PLT is less than 20. After the result of the platelet re-detection is obtained, a second platelet detection result of the sample is generated, and the user can publish the report with the first or second detection result. Moreover, the method in Scenario II is not limited to retesting, and PLT-O detection and RET detection with increased statistical amount can be performed in the RET detection area directly after acquiring low platelet count information.

Details are given below:
Scenario I

Figure 3:
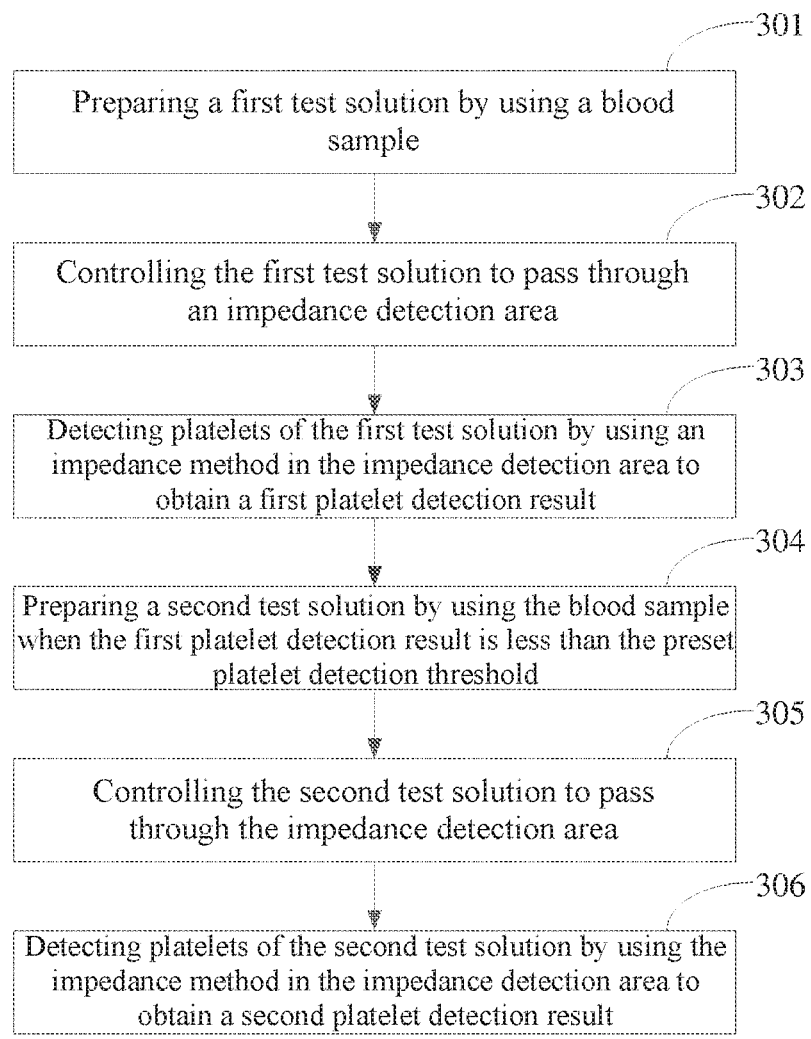
FIG. 3 is a method flowchart of a blood testing method provided by another embodiment of the present disclosure.

Referring to FIG. 3, it is a method flowchart of a blood testing method provided by an embodiment of the present disclosure. The blood testing method can be applied to the blood testing apparatus shown in FIG. 1. The blood testing method of the embodiment of the present disclosure includes the following steps:

Step 301: preparing a first test solution by using a blood sample.

The blood testing apparatus prepares the first test solution using the blood sample acquired, and the first test solution is configured for detection of the platelet count in the embodiment of the present disclosure.

For example, after a user provides a blood sample to the blood testing apparatus through a sampling tube, the apparatus draws the blood sample from the sampling tube to a reaction tank and draws a reagent to the reaction tank so that the blood sample and the reagent react in the reaction tank to obtain the first test solution. The reagent contains no dye.

Step 302: controlling the first test solution to pass through an impedance detection area.

The impedance detection area can also be referred to as a PLT-I channel in the embodiment of the present disclosure. In the impedance detection area, the blood testing apparatus can use the impedance method to detect platelets in the first test solution, and the impedance method can also be referred to as a PLT-I detection method.

In an embodiment of the present disclosure, the impedance detection area may be a detection area using the Coulter principle or sheath flow impedance. The impedance detection area through which the first test solution passes may be such that platelets pass through the impedance detection area one at a time under the action of a micro-orifice or sheath fluid. Because the reagent in the reaction tank charges the platelets of the first test solution, the platelets of the first test solution generate impedance signals in the impedance detection area.

For example, as shown in FIG. 1, the blood testing apparatus draws the first test solution in the reaction tank into the sample preparation tube, and then pressurizes the sample preparation tube through the sample injector, so that the first test solution is pushed into the detection area in the detector, and thus the first test solution passes through the detection area for PLT detection. The detection area is an impedance detection area for PLT detection by the impedance method. The detector can also be referred to as a counting tank.

Step 303: detecting platelets of the first test solution by using an impedance method in the impedance detection area to obtain a first platelet detection result.

The blood testing apparatus controls the first test solution to pass through the impedance detection area, so that the blood testing apparatus can perform platelet detection on the first test solution by using the impedance method in the impedance detection area, namely perform PLT-I detection on the first test solution, and the detection result is the first platelet detection result.

After obtaining the first platelet detection result, the blood testing apparatus can output the first platelet detection result to inform the user of the detection result.

For example, when the blood testing apparatus controls the first test solution to pass through the impedance detection area, platelets of the first test solution pass through the detection area of the detector one at a time and generate impedance signals in the detection area. By acquiring the impedance signals, the blood testing apparatus can realize platelet detection on the first test solution, and according to the impedance signals, the blood testing apparatus can calculate the first platelet detection result of the first test solution. The first platelet detection result reflects the platelet content of the blood sample.

Step 304: preparing a second test solution by using the blood sample when the first platelet detection result is less than the preset platelet detection threshold. The preset platelet detection threshold is a threshold for determining whether the platelet content of the blood sample is low.

After obtaining the first platelet detection result, the blood testing apparatus determines whether the first platelet detection result is less than a preset platelet detection threshold. If the first platelet detection result is less than the preset platelet detection threshold, it is indicated that the platelet content of the blood sample is abnormal and is of a low platelet count, and therefore the platelet content of the blood sample needs to be remeasured to obtain an accurate platelet detection result. To this end, the blood sample testing apparatus uses the blood sample from which the first test solution was prepared to prepare the second test solution for platelet detection, it should be noted that the second test solution and the first test solution are derived front the blood sample of the same user to be tested, and the second test solution can be prepared using the blood sample remaining after preparing the first test solution.

It can be understood that if the first platelet detection result is greater than or equal to the preset platelet detection threshold, then the blood sample is a blood sample with non-low platelet content, and in this case, the blood testing apparatus can output the first platelet detection result.

The specific implementation of step 301 above can be referred to for the specific method for the blood testing apparatus to prepare the second test solution using the blood sample.

For example, after the blood testing apparatus performs platelet detection on the first test solution, the obtained first platelet detection result is PLT=40 and the preset platelet detection threshold is 50, so that the blood testing apparatus determines that the first platelet detection result is less than the preset platelet detection threshold. Then, the blood testing apparatus draws the blood sample from the sampling tube in step 301 into the reaction tank, and draws the reagent into the reaction tank, so that the blood sample and the reagent react to produce the second test solution. The second test solution is suitable for platelet detection using the impedance method.

In some embodiments of the present disclosure, sufficient first test solution can be prepared in step 301. When the first test solution is used to perform step 303, a portion of the first test solution may remain in the blood testing apparatus. In this case, when the first platelet detection result is less than the preset platelet detection threshold, the blood testing apparatus can draw the second test solution from the remaining test solution of the first test solution. For example, a test solution is drawn from the remaining test solution of the first test solution in the reaction tank, and the drawn test solution is the second test solution for performing the following steps. That is, the second test solution may be prepared anew using the blood sample or may be obtained from the remaining test solution of the first test solution.

It can be understood that the preset platelet detection threshold of the embodiment of the present disclosure can be preset by the blood testing apparatus or can be specifically set by the user. Since the criteria for a blood sample to be considered as being of a low platelet count may vary for different users, in some embodiments of the present disclosure, before detecting platelets of the first test solution by using an impedance method in the impedance detection area, the method of the embodiments of the present disclosure further includes: acquiring a platelet detection threshold input by a user. Therefore, the user can customize the setting of a platelet detection threshold for determining a low platelet count. Thus, step 304 specifically comprises: preparing a second test solution by using the blood sample or by aspirating the remaining test solution of the first test solution when the first platelet detection result is less than the platelet detection threshold. Therefore, the user can set a platelet detection threshold for determining a low platelet count according to actual needs so as to meet the detection requirements of different users.

Step 305: controlling the second test solution to pass through the impedance detection area; and after obtaining the second test solution, the blood testing apparatus controlling the second test solution to pass through the impedance detection area, which is a detection area for platelet detection by using the impedance method, and the impedance detection area can be referred to as a PIT-I detection area. The impedance detection area of step 305 and the impedance detection area of step 302 may be the same detection area.

The detailed description of step 302 can be referred to for specific implementation of step 305.

Step 306: detecting platelets of the second test solution by using the impedance method in the impedance detection area to obtain a second platelet detection result.

A statistical amount of the second test solution passing through the impedance detection area is greater than a statistical amount of the first test solution passing through the impedance detection area. The statistical amount is the amount of the test solution used by the blood testing apparatus for statistics.

When the blood testing apparatus controls the second test solution to pass through the impedance detection area, platelet detection is carried out on the second test solution by using an impedance method in the impedance detection area to obtain a second platelet detection result. Since the statistical amount of the second test solution passing through the impedance detection area is greater than the statistical amount of the first test solution passing through the impedance detection area, the statistical amount of platelets increases, so that the second platelet detection result obtained by the blood testing apparatus using the second test solution will be more accurate.

In some embodiments of the present disclosure, after step 306, the blood testing method of the embodiments of the present disclosure further comprises: the blood testing apparatus outputting the second platelet detection result so that the user can get to know the second platelet detection result. Alternatively, the blood testing apparatus outputs a second platelet detection result and a preset mark for marking the second platelet detection result. In this way, the user can know according to the preset mark that the second platelet detection result is a detection result obtained after a retest for a low platelet count.

In some embodiments of the present disclosure, after step 306, the blood testing apparatus may not output the second platelet detection result, but may perform other operations using the second platelet detection result as a triggering condition.

It should be noted that the blood testing apparatus controls in such a manner that a statistical amount of the second test solution passing through the impedance detection area is greater than a statistical amount of the first test solution passing through the impedance detection area. As it is known from the determination in step 304 that the platelet content of the blood sample is of a low platelet count, it is necessary to increase the statistical amount of platelets when detecting the platelet content of the blood sample in order to obtain a more accurate platelet detection result of the blood sample. Therefore, the statistical amount of the second test solution passing through the impedance detection area is greater than the statistical amount of the first test solution passing through the impedance detection area, and thus the blood testing apparatus can measure the low platelet count accurately by using the second test solution. In order to achieve this goal, there are many particular ways for implementation. Here are a few examples among them, as follows:

Example I

Increasing Statistical Time Period

In the above steps, steps 303 and 306 are specifically defined.

Step 303 specifically comprises: detecting platelets of the first test solution by using the impedance method in the impedance detection area within a first time period.

Step 306 specifically comprises: detecting platelets of the second test solution by using the impedance method in the impedance detection area within a second time period. The second time period is greater than the first time period. That is, the method of the embodiment of the present disclosure increases the statistical amount of the test solution by increasing the detection time for the test solution. So long as the statistical time for the second test solution is greater than the statistical time for the first test solution, the statistical amount of the second test solution will be greater than the statistical amount of the first test solution.

It can be understood that in order to realize the method of Example I, the blood testing apparatus needs to provide a greater amount of the second test solution to the impedance detection channel than that of the first test solution. In some embodiments of the present disclosure, different volume metering tubes may be provided for the first test solution and the second test solution, respectively, for volume metering. In the embodiment using sheath fluid, the blood testing apparatus can provide enough sheath fluid for compressing platelets of the test solution so that platelets with different passage time durations can pass through the impedance detection area one by one.

Example II

Increasing Speed of Passage

Step 302 specifically comprises: controlling the first test solution to pass through the impedance detection area at a first rate.

Step 305 specifically comprises: controlling the second test solution to pass through the impedance detection area at a second rate.

The second rate is greater than the first rate. In this way, by increasing the rate of the test solution passing through the impedance detection area, the blood testing apparatus can increase the statistical amount of platelets in the test solution with the statistical time unchanged.

The embodiment of example II can be realized by increasing the pushing speed of the injector to push the second test solution relative to that of the first test solution, or by making the concentration of the second test solution greater than the concentration of the first test solution when preparing the test solutions. Since platelets pass through the impedance detection area one at a time, when the pushing speed of the injector is unchanged, the speed of platelets of the second test solution passing through the impedance detection area is greater than the passing speed of platelets of the first test solution.

It can be understood that in some embodiments of the present disclosure, the blood testing apparatus can use the fluorescence method to detect platelets in addition to the impedance method. After step 304, the above method uses the impedance method to detect platelets in the second test solution. In some embodiments of the present disclosure, in addition to setting the threshold of a low platelet count, other conditions can be added to determine the detection method to be used in the platelet retest.

Specifically, when the first platelet detection result is less than a preset platelet detection threshold, the blood sample can be tested with regard to red blood cells, so as to determine a retest method of platelets based on the test result of red blood cells, for example:

The specific implementation of step 304 is as follows: preparing a second test solution by using the blood sample or by aspirating the remaining test solution of the first test solution when the first platelet detection result is less than a preset platelet detection threshold and no abnormal detection information of red blood cell of the blood sample is acquired.

That is, when the red blood cell detection of the blood sample is normal, the platelet of the blood sample is remeasured using the PLT-I method, that is, the above steps are executed. When a detection result of the red blood cell of the blood sample is abnormal, the platelet is remeasured using optical detection, and RET detection is simultaneously performed. The method of the embodiment of the present disclosure further comprises:

Step A1: preparing a third test solution by using the blood sample when the first platelet detection result is less than a preset platelet detection threshold and abnormal detection information of red blood cell of the blood sample is acquired.

The preset platelet detection threshold is a threshold for determining whether the platelet content of the blood sample is low.

After obtaining the first platelet detection result, the blood testing apparatus determines whether the first platelet detection result is less than a preset platelet detection threshold. If the first platelet detection result is less than the preset platelet detection threshold, it is indicated that the platelet content of the blood sample is abnormal and is of a low platelet count, and therefore the platelet content of the blood sample needs to be remeasured to obtain an accurate platelet detection result. If the red blood cell detection abnormality information of the blood sample is also obtained, RET detection needs to be performed on the blood sample. Therefore, in this case, a third test solution can be prepared using the blood sample, so as to perform optical detection on the third test solution.

There are many ways of implementation for the blood testing apparatus to obtain red blood cell detection abnormality information of the blood sample. For example, the blood testing apparatus uses the blood sample to prepare other test solutions, and then performs red blood cell-related detection on the test solutions in other channels to obtain red blood cell-related detection results. The red blood cell detection abnormality information comprises but is not limited to RBC (red blood cell count) less than a preset value, HGB (hemoglobin determination) less than another preset value, RDW-CV (red blood cell distribution width-corpuscular volume) greater than another preset value, or a certain red blood cell related alarm, such as an anemia alarm, etc. The acquisition of red blood cell detection abnormality information indicates that RET detection is required for the blood sample.

The detailed description of step 404 below can be further referred to for specific implementation of step A1. The third test solution in step A1 is the second test solution in step 404.

Optionally, the preset platelet detection threshold in step A1 may be higher than the preset platelet detection threshold in step 304.

Step A2: controlling the third test solution to pass through an RET detection area.

Step A3: performing an optical detection on the third test solution in the RET detection area to obtain an RET detection result and a third platelet detection result, where the statistical amount of the third test solution passing through the RET detection area is greater than a preset statistical amount.

The statistical amount of the third test solution passing through the RET detection area is greater than a preset statistical amount. The statistical amount is the amount of the test solution used by the blood testing apparatus for statistics. RET detection results include but are not limited to RET (reticulocyte percentage), RET # (absolute reticulocyte count), MRV/MCVR (mean reticulocyte volume), RMI (reticulocyte maturation index), and other RET-related parameters.

The blood testing apparatus performs optical detection on the third test solution in the RET detection area and thus can obtain the RET detection result and the third platelet detection result. Then, the blood testing apparatus can output the RET detection result and the third platelet detection result.

Because in step A1, it is determined that the blood sample is a blood sample of a low platelet count, in order to improve the detection accuracy of the third test solution of the blood sample, it is necessary to increase the statistical amount of the third test solution. The statistical amount of the third test solution passing through the RET detection area is greater than a preset statistical amount. The preset statistical amount is the preset statistical amount used in normal PLT-O detection, which can be performed in normal platelet samples.

The detailed description of step 406 below can be referred to for specific implementation of step A3.

For red blood cell detection of blood samples, red blood cell detection abnormality information, and implementation of steps A1 to A3, details are given in the corresponding detailed description in Scenario II below.

In summary, the blood testing method of the embodiment of the present disclosure controls the first test solution to pass through the impedance detection area after preparing the first test solution using the blood sample, thereby detecting platelets of the first test solution by using an impedance method in the impedance detection area to obtain a first platelet detection result. Then, a second test solution is prepared by using the blood sample or the second test solution is drawn from the remaining test solution of the first test solution when the first platelet detection result is less than a preset platelet detection threshold. Next, the second test solution is controlled to pass through the impedance detection area, and platelet detection is carried out on the second test solution by using an impedance method in the impedance detection area to obtain a second platelet detection result. A statistical amount of the second test solution passing through the impedance detection area is greater than a statistical amount of the first test solution passing through the impedance detection area. In this way, when a low platelet count of a sample is detected by the impedance method, the platelet detection is re-conducted using the test solution of the blood sample, and the platelet are detected again by the impedance method in the impedance detection area with an increased statistical amount of the test solution, thereby obtaining a second platelet detection result. By the PLT-I detection with an increased statistical amount, the detection accuracy of PLT-I can be improved, i.e. the second platelet detection result is more accurate. The method of the embodiment of the present disclosure is particularly useful for instruments equipped without or not switching on an optical RET or optical PLT channel. Being independent of fluorescence detection, the instruments have reduced manufacturing costs and usage costs while maintaining high detection accuracy.

In order to more intuitively understand the steps involved in the above Scenario I, a specific usage scenario is provided for the method of the embodiment of the present disclosure as follows:

A platelet detection threshold input by a user to the blood testing apparatus is $20*10^9/L$. Then, the blood testing apparatus uses the obtained blood sample to prepare a first test solution, and the blood testing apparatus carries out platelet detection on the first test solution by using an impedance method in the impedance detection area to obtain a first platelet detection result. The blood testing apparatus can output the first platelet detection result, and can alternatively output the first platelet detection result only if the first platelet detection result is greater than or equal to $20*10^9/L$. However, when the first platelet detection result is less than $20*10^9/L$, the blood testing apparatus uses the blood sample to prepare a second test solution for retesting the platelet count. Then, the blood testing apparatus controls the second test solution to pass through the impedance detection area, and carries out platelet detection on the second test solution by using an impedance method in the impedance detection area to obtain a second platelet detection result. The blood testing apparatus outputs the second platelet detection result.

The blood testing method provided in Scenario I is to increase statistical amount of the reagent when a low platelet count is detected, and to retest platelets in the test solution by the impedance method. The embodiment of the present disclosure also provides a blood testing method, which is configured for performing RET detection and PTL-O detection with an increased statistical amount in an RET channel at once when a low platelet count is detected. Details are described below.

Scenario II

Figure 4:
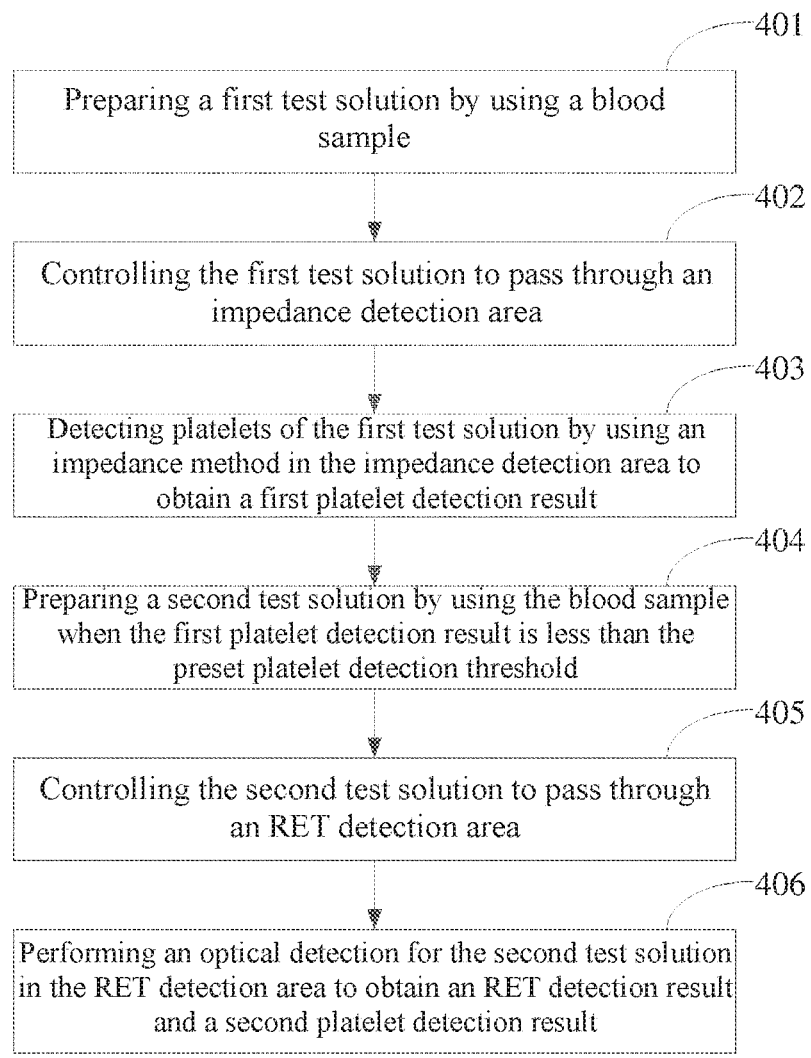
FIG. 4 is a method flowchart of a blood testing method provided by another embodiment of the present disclosure.

Referring to FIG. 4, it is a method flowchart of a blood testing method provided by an embodiment of the present disclosure. The method can be applied to the blood testing apparatus shown in FIGS. 1 and 2 above, and the blood testing method of the embodiment of the present disclosure comprises:

Step 401: preparing a first test solution by using a blood sample.

The user provides the blood sample for the blood testing apparatus. The blood testing apparatus can prepare the first test solution using the blood sample, and the first test solution is configured for measurement of the platelet count.

For example, after a user provides a blood sample to the blood testing apparatus through a sampling tube, the apparatus draws the blood sample from the sampling tube to a reaction tank and draws a reagent to the reaction tank so that the blood sample and the reagent react in the reaction tank to obtain the first test solution. The reagent is a reagent related to platelet detection. The first test solution is a test solution suitable for platelet detection by using the impedance method.

Step 402: controlling the first test solution to pass through an impedance detection area.

The blood testing apparatus is provided with a detector having a target detection area in which platelet detection can be performed. Therefore, after the first test solution is prepared, the blood testing apparatus controls the first test solution to pass through the target detection area.

The detailed description of step 302 can be referred to for specific implementation of step 402.

Step 403: detecting platelets of the first test solution by using an impedance method in the impedance detection area to obtain a first platelet detection result.

The blood testing apparatus controls the first test solution to pass through the impedance detection area, so that the platelet detection can be carried out on the first test solution in the impedance detection area to obtain the first platelet detection result. After obtaining the first platelet detection result, the blood testing apparatus can output the first platelet detection result to inform the user of the detection result. The low platelet detection by impedance method can also be referred to as PLT-I detection.

The detailed description of step 303 can be referred to for specific implementation of step 403.

Step 404: preparing a second test solution by using the blood sample when the first platelet detection result is less than the preset platelet detection threshold.

The preset platelet detection threshold is a threshold for determining whether the platelet content of the blood sample is low.

After obtaining the first platelet detection result, the blood testing apparatus determines whether the first platelet detection result is less than a preset platelet detection threshold. If the first platelet detection result is less than the preset platelet detection threshold, it is indicated that the platelet content of the blood sample is abnormal and is of a low platelet count, and therefore the platelet content of the blood sample needs to be remeasured to obtain an accurate platelet detection result. To this end, the blood sample from which the first test solution was prepared is used to prepare the second test solution for platelet detection. The second test solution is a test solution suitable for platelet detection and RET detection in RET detection area. The second test solution and the first test solution are derived from the blood sample of the same user to be tested. The second test solution can be prepared using the blood sample remaining after preparing the first test solution.

For example, after the blood testing apparatus performs platelet detection on the first test solution, the obtained first platelet detection result is PLT=40 and the preset platelet detection threshold is 50, so that the blood testing apparatus determines that the first platelet detection result is less than the preset platelet detection threshold. Then, the blood testing apparatus draws the blood sample from the sampling tube in step 401 into another reaction tank, and draws another reagent into the reaction tank, so that the blood sample and the reagent react to produce the second test solution. The reagent for preparing the second test solution is a reagent that enables RET detection and PLT-O detection on the blood sample in the RET detection area. The second test solution is a test solution suitable for platelet detection and RET detection in RET detection area.

In the embodiment of the present disclosure, the following step 406 performs platelet detection on the second test solution by a fluorescence method, and the platelet detection by the fluorescence method can also be referred to as PLT-O detection. The principle is that in the RET channel, fluorescent dye is used to bind with RNA in platelets, and then flow cytometry is used to excite fluorescence of corresponding wavelength for detection. At the same time, red blood cells and fragments thereof can be distinguished from platelets because red blood cells and fragments thereof have no RNA and thus do not bind with fluorescent dye, and therefore the problem that PLT detection is prone to interference can be solved.

Therefore, platelets in the second test solution prepared in step 404 have been binded with fluorescent dye to prepare for the following steps.

It can be understood that the above steps 401 to 404 are one of the specific implementations of preparing a second test solution by using the blood sample when low platelet count information of the blood sample is obtained.

In the method of the embodiment of the present disclosure, once the blood testing apparatus obtains low platelet count information of the blood sample, the second test solution can be prepared using the blood sample. The low platelet count information indicates that a platelet content of the blood sample is less than a preset platelet detection threshold. For example, in the above-mentioned step 404, the blood testing apparatus determines that the first platelet detection result is less than the preset platelet detection threshold, that is, low platelet count information of the blood sample is obtained.

In some embodiments of the present disclosure, acquisition of low platelet count information of the blood sample by the blood testing apparatus can also be realized in other ways. For example, the user selects a low platelet count detection mode in the blood testing apparatus, and acquisition of this selection information by the blood testing apparatus is acquisition of the low platelet count information of the blood sample. Alternatively, when other apparatus detects that the blood sample has a platelet content less than a preset platelet detection threshold through the above-mentioned method, an indication of a low platelet count is sent to the blood testing apparatus, and the acquisition of the indication of the low platelet count by the blood testing apparatus is acquisition of the low platelet count information of the blood sample.

In some embodiments of the present disclosure, since step 406 is performed by performing RET detection and PLT-O detection on the second test solution, in order to make the RET detection more adapted for actual needs, other triggering conditions may be set for retest of the blood sample. For example, step 404 specifically includes: preparing a second test solution by using the blood sample when the first platelet detection result is less than a preset platelet detection threshold and abnormal detection information of red blood cell of the blood sample is acquired.

When red blood cell abnormality information in a blood sample is detected, RET detection is even more necessary for the blood sample, and the first platelet detection result is less than the preset platelet detection threshold, which indicates that the blood sample is a low platelet count sample and needs to be remeasured for platelets. When the above two conditions are both met, the execution of step 406 can better meet the detection requirements of the user, thereby reasonably using the detection method, reducing the usage cost and improving the detection efficiency.

There are many ways of implementation for the blood testing apparatus to obtain red blood cell detection abnormality information of the blood sample. For example, the blood testing apparatus uses the blood sample to prepare other test solutions, and then performs red blood cell-related detection on the test solutions in other channels to obtain red blood cell-related detection results. The red blood cell detection abnormality information comprises but is not limited to RBC (red blood cell count) less than a preset value, HGB (hemoglobin determination) less than another preset value, RDW-CV (red blood cell distribution width-corpuscular volume) greater than another preset value, or a certain red blood cell related alarm, such as an anemia alarm, etc. The acquisition of red blood cell detection abnormality information indicates that RET detection is required for the blood sample.

In this way, in some embodiments of the present disclosure, after the blood testing apparatus switches on the RET channel, if it is determined that the sample with the current result needs to be remeasured according to the retest triggering condition, for example, red blood cell detection abnormality information is acquired, then the blood testing apparatus checks whether the PLT-I of the current sample is low, i.e., steps 401 to 404 described above are performed; and if the PLT-I detection result of the current sample is low, the following steps are performed to obtain the RET detection result and the second platelet detection result.

It can be understood that in the above two parallel implementations of step 404, namely, in the first implementation of "preparing a second test solution by using the blood sample when the first platelet detection result is less than the preset platelet detection threshold", and the second implementation of "preparing a second test solution by using the blood sample when the first platelet detection result is less than a preset platelet detection threshold and abnormal detection information of red blood cell of the blood sample is acquired", the "preset platelet detection threshold" in the second implementation may be higher than the "preset platelet detection threshold" in the first implementation.

It can be understood that the preset platelet detection threshold of the embodiment of the present disclosure can be preset by the blood testing apparatus or can be specifically set by the user. Since the criteria for a blood sample to be considered as being of a low platelet count may vary for different users, in some embodiments of the present disclosure, before detecting platelets of the first test solution by using an impedance method in the impedance detection area, the method of the embodiments of the present disclosure further comprises: acquiring a platelet detection threshold input by a user. Thus, step 404 specifically comprises: preparing a second test solution by using the blood sample when the first platelet detection result is less than the platelet detection threshold input by the user. Therefore, the user can set a platelet detection threshold for determining a low platelet count according to actual needs so as to meet the detection requirements of different users.

It can be understood that in some embodiments of the present disclosure, the specific type of red blood cell detection abnormality information involved in triggering the retest can also be preset by the user.

In some embodiments of the present disclosure, step 404 may be implemented in other ways. For example, step 404 may be: preparing a third test solution by using the blood sample when the first platelet detection result is less than the preset platelet detection threshold. The third test solution is a test solution for platelet detection by using the impedance method. Then, the third test solution is controlled to pass through an impedance detection area, and platelet detection is carried out on the third test solution by using an impedance method in the impedance detection area to obtain a third platelet detection result. In addition, a statistical amount of the third test solution passing through the impedance detection area is greater than a statistical amount of the first test solution passing through the impedance detection area. That is, steps 305 and 306 of the above-described embodiment shown in FIG. 3 are performed using the third test solution. When the third platelet detection result is less than a preset platelet detection threshold, the blood sample is used to prepare a second test solution, and the second test solution is a test solution for optical detection. Then, steps 405 and 406 are performed using the second test solution. In this way, the chance of triggering steps 405 and 406 can be reduced, thereby saving reagents of optical detection. It should be noted that the first test solution, the second test solution and the third test solution here are solutions from the same blood sample.

Step 405: controlling the second test solution to pass through an RET detection area.

After obtaining the second test solution, the blood testing apparatus controls the second test solution to pass through the RET detection area, where RET detection and PLT-O detection can be performed. For the blood testing apparatus comprising the REF detection area, reference can be made to the embodiment shown in FIG. 2.

Step 406: performing an optical detection on the second test solution in the RET detection area to obtain an RET detection result and a second platelet detection result.

The statistical amount of the second test solution passing through the RET detection area is greater than a preset statistical amount. The statistical amount is the amount of the test solution used by the blood testing apparatus for statistics. RET detection results include but are not limited to RET (reticulocyte percentage), RET # (absolute reticulocyte count), MRV/MCVR (mean reticulocyte volume), RMI (reticulocyte maturation index), and other RET-related parameters.

The blood testing apparatus performs optical detection on the second test solution in the RET detection area and thus can obtain the RET detection result and the second platelet detection result. Then, the blood testing apparatus can output the RET detection result and the second platelet detection result.

Because in step 404, it is determined that the blood sample is a blood sample of a low platelet count, in order to improve the detection accuracy of the second test solution of the blood sample, it is necessary to increase the statistical amount of the second test solution. The statistical amount of the second test solution passing through the RET detection area is greater than a preset statistical amount. The preset statistical amount is the statistical amount used in normal PLT-O detection, which can be the detection when the blood sample is not set as a low platelet count sample.

In order to make the statistical amount of the second test solution passing through the RET detection area greater than the preset statistical amount, there may be various implementations. For example, step 406 specifically comprises: performing the optical detection on the second test solution in the RET detection area within a target time period to obtain an RET detection result and a second platelet detection result. The target time period is greater than a preset time period, and the preset time period corresponds to the preset statistical amount. That is, the statistical amount of test solution is increased by increasing the statistical time period of PLT-O detection. In this way, while RET measurement is triggered, the measurement time is increased to obtain increased statistical amount for PLT-O, thus obtaining RET related parameters and increased statistical amount of PLT at once. With reference to Example II of Scenario I above, the embodiment of the present disclosure can also increase the statistical amount of the second test solution by increasing the speed of the test solution passing through the RET detection area, that is, the blood testing apparatus controls the second test solution to pass through the RET detection area at a target speed that is greater than a preset speed at which the blood testing apparatus controls the test solution to pass through the RET detection area during normal PLT-O detection.

According to the blood testing method of the embodiment of the present disclosure, the RET detection result and PLT detection result can be obtained at once in the RET channel, so that the detection efficiency is improved and the consumption of the sample is reduced. As the number of red blood cells in the test solution is more than that of platelets, when the platelet count is low, it is necessary to increase the statistical amount of the test solution to improve the detection accuracy of platelets. However, it is not necessary to use less statistical amount for detecting red blood cells than for detecting platelets. Therefore, in some embodiments of the present disclosure, different processing methods can be performed on the RET detection result and PUT detection result. Specifically, step 406 specifically includes the following steps:

step B1: performing optical detection on the second test solution in the RET detection area.

Step B2: collecting and storing a first light scatter signal and a first fluorescence signal of cells in the second test solution one by one within a first detection time period.

Step B3: collecting a second light scatter signal and a second fluorescence signal of cells in the second test solution one by one within a second detection time period, determining whether intensity of scattered light of the second light scatter signal is greater than or equal to a preset intensity threshold, and stopping storing the second light scatter signal and the second fluorescence signal if the intensity of scattered light of the second light scatter signal is greater than or equal to the preset intensity threshold; storing the second light scatter signal and the second fluorescence signal if the intensity of scattered light of the second light scatter signal is less than the preset intensity threshold.

Step B4: calculating an RET detection result according to the first light scatter signal and the first fluorescence signal stored within the first detection time period.

Step B5: calculating a second platelet detection result according to the first light scatter signal and the first fluorescence signal stored within the first detection time period and the second light scatter signal and the second fluorescence signal stored within the second detection time period. Within the first detection time period and the second detection time period, the statistical amount of the second test solution passing through the RET detection area is greater than the preset statistical amount.

In this way, the blood testing apparatus performs optical detection on the second test solution in the RET detection area. In this case, light scatter signals and fluorescence signals are generated in the RET detection area, that is, under the irradiation of a light source, each of the cells in the second test solution passing through the RET detection area generates light scatter signals and fluorescence signals. For these light scatter signals and fluorescence signals, the blood testing apparatus performs different processing methods in different detection time periods. In the first detection time period, light scatter signals and first fluorescence signals of each cell, including red blood cells, reticulocytes and platelets, are collected and stored. Due to the large number of red blood cells and reticulocytes, sufficient data for calculation is already obtained within the first detection time period, so that in a detection time period other than the first detection time period, signals of reticulocytes may not be stored, but signals are still stored for platelets which have a small number.

In the second detection time period, light scatter signals and fluorescence signals of cells are collected, but an operation of comparing the scattered light intensity of the light scatter signals with a preset intensity threshold needs to be performed. If the scattered light intensity of the light scatter signals is greater than or equal to the preset intensity threshold, indicating that the cells to which the light scatter signals and fluorescence signals belong may be reticulocytes or leukocytes, then the storage of the light scatter signals and fluorescence signals is stopped; and otherwise, the cells to which the light scatter signals and fluorescence signals belong may be platelets, and the light scatter signals and fluorescence signals generated by platelets still need to be stored for use in calculation.

The blood testing apparatus obtains enough signals for calculating the REF detection result in the first detection time period, so that optical signals of RET need not be stored in other detection time periods. Therefore, it not only makes the RET detection result meet the use requirements, but also avoids the excessive amount of data obtained by RET detection and thus unnecessary redundant data. In order to carry out accurate PLT-O detection, the blood testing apparatus needs to acquire optical signals of platelets in the first detection time period and the second detection time period.

In this way, the RET detection result can be calculated using light scatter signals and fluorescence signals stored within the first detection time period. A second platelet detection result is calculated using the light scatter signal and the fluorescence signal stored within the first detection time period and the light scatter signal and the fluorescence signal stored within the second detection time period.

It can be understood that the sequence of the first detection time period and the second detection time period is not specifically defined in the embodiment of the present disclosure.

Optionally, the first light scatter signal and the second light scatter signal are forward scatter (FSC) signals.

Optionally, within the first detection time period, the statistical amount of the second test solution passing through the RET detection area is a preset RET statistical amount.

In order to more intuitively understand the steps involved in the above Scenario II, a specific usage scenario is provided for the method of the embodiment of the present disclosure as follows:

A platelet detection threshold input by a user to the blood testing apparatus is $20*10^9$/L. Then, the blood testing apparatus uses the obtained blood sample to prepare a first test solution, and the blood testing apparatus carries out platelet detection on the first test solution by using an impedance method in the impedance detection area to obtain a first platelet detection result. The blood testing apparatus can output the first platelet detection result, and can alternatively output the first platelet detection result only if the first platelet detection result is greater than or equal to $20*10^9$/L. However, when the first platelet detection result is less than $20*10^9$/L, the blood testing apparatus uses the blood sample to prepare a second test solution. In this case, if the blood testing apparatus also obtains red blood cell detection abnormality information of the blood sample, for example, the blood testing apparatus detects that the RBC count (red blood cell count) of the blood sample is less than a preset red blood cell count value, then, the blood testing apparatus controls the second test solution to pass through the RET detection area, thereby performing optical detection on the second test solution in the RET detection area to obtain an RET detection result and a second platelet detection result. Then, the blood testing apparatus outputs the RET detection result and the second platelet detection result. Thus, the user gets to know the RET detection result and the second platelet detection result of the blood sample.

In summary, in the blood testing method of the embodiment of the present disclosure, a second test solution is prepared by using the blood sample when low platelet count information of the blood sample is obtained, where the low platelet count information indicates that a platelet content of the blood sample is less than a preset platelet detection threshold. Then, the second test solution is controlled to pass through an RET detection area, performing the optical detection on the second test solution in the RET detection area to obtain an RET detection result and a second platelet detection result, where the statistical amount of the second test solution passing through the RET detection area is greater than a preset statistical amount. The method of the embodiment of the present disclosure is suitable for instruments equipped with and switching on an optical RET channel. When a blood sample acquired is a low platelet count sample, optical detection is carried out on platelets and RETs of the blood sample by using a test solution of an increased statistical amount in the RET detection area, which improves the accuracy of platelet detection as well as the detection efficiency, since the RET detection and PLT-O detection are completed at once to obtain the RET detection result and PLT detection result simultaneously, thus reducing the consumption of samples and reagents and lowering the costs.

Figure 5:
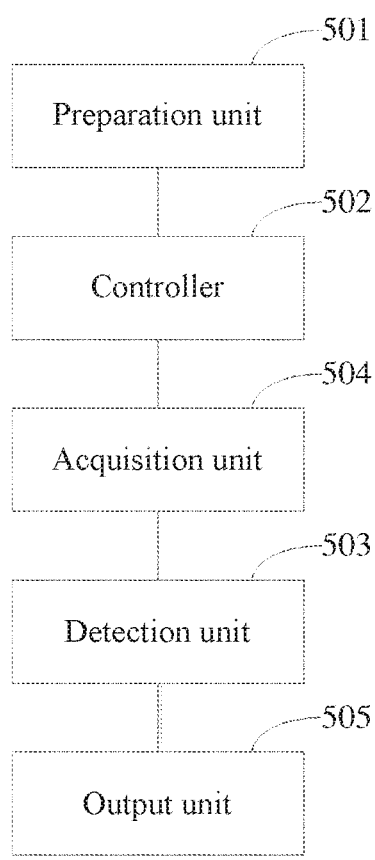
FIG. 5 is a schematic structure diagram of a blood testing apparatus provided by another embodiment of the present disclosure.

FIG. 5 is a schematic structure diagram of a blood testing apparatus provided by an embodiment of the present disclosure, which can be integrated in the blood testing apparatus shown in FIG. 1 above, and the blood testing apparatus of the embodiment of the present disclosure can perform the blood testing method shown in scenario I above.

Referring to FIG. 5, the blood testing apparatus includes a preparation unit 501 configured for preparing a first test solution by using a blood sample, a controller 502 configured for controlling the first test solution to pass through an impedance detection area, and a detection unit 503 configured for detecting platelets of the first test solution by using an impedance method in the impedance detection area to obtain a first platelet detection result. The preparation unit 501 is further configured for preparing a second test solution by using the blood sample or by aspirating the remaining test solution of the first test solution when the first platelet detection result is less than a preset platelet detection threshold. The controller 502 is further configured for controlling the second test solution to pass through the impedance detection area.

The detection unit 503 is further configured for detecting platelets of the second test solution by using an impedance method in the impedance detection area to obtain a second platelet detection result. A statistical amount of the second test solution passing through the impedance detection area is greater than a statistical amount of the first test solution passing through the impedance detection area.

Optionally, the detection unit 503 is further configured for detecting platelets of the first test solution by using the impedance method in the impedance detection area within a first time period;

the detection unit 503 is further configured for detecting platelets of the second test solution by using the impedance method in the impedance detection area within a second time period, where the second time period is greater than the first time period.

Optionally, the apparatus further includes an acquisition unit 504 configured for acquiring a platelet detection threshold input by a user, the preparation unit 501 is further configured for preparing a second test solution by using the blood sample or by aspirating the remaining test solution of the first test solution when the first platelet detection result is less than the platelet detection threshold.

Optionally, the preparation unit 501 is further configured for preparing a second test solution by using the blood sample or by aspirating the remaining test solution of the first test solution when the first platelet detection result is less than a preset platelet detection threshold and no abnormal detection information of red blood cell of the blood sample is acquired. The preparation unit 501 is further configured for preparing a third test solution by using the blood sample when the first platelet detection result is less than a preset platelet detection threshold and abnormal detection information of red blood cell of the blood sample is acquired. The controller 502 is further configured for controlling the third test solution to pass through an RET detection area. The detection unit 503 is further configured for performing optical detection on the third test solution in the RET detection area to obtain an RET detection result and a third platelet detection result, where the statistical amount of the third test solution passing through the RET detection area is greater than a preset statistical amount.

Optionally, the blood testing apparatus of the embodiment of the present disclosure further comprises an output unit 505. The output unit 505 is configured for outputting the second platelet detection result; or, outputting the second platelet detection result and a preset mark, where the preset mark is configured for marking the second platelet detection result.

In summary, in the blood testing apparatus, the preparation unit 501 prepares a first test solution by using a blood sample; the controller 502 then controls the first test solution to pass through the impedance detection area; and the detection unit 503 carries out platelet detection on the first test solution by using an impedance method in the impedance detection area to obtain a first platelet detection result. The preparation unit 501 prepares the second test solution by using the blood sample or draws the second test solution from the remaining test solution of the first test solution when the first platelet detection result is less than the preset platelet detection threshold. The controller 502 controls the second test solution to pass through the impedance detection area, so that the detection unit 503 carries out platelet detection on the second test solution by using an impedance method in the impedance detection area to obtain a second platelet detection result, where a statistical amount of the second test solution passing through the impedance detection area is greater than a statistical amount of the first test solution passing through the impedance detection area. In this way, when a low platelet count of a sample is detected by the impedance method, the platelet detection is re-conducted using the test solution of the blood sample, and the platelet are detected again by the impedance method in the impedance detection area with an increased statistical amount of the test solution, thereby obtaining a second platelet detection result. By the PLT-I detection with an increased statistical amount, the detection accuracy of PLT-I can be improved, i.e. the second platelet detection result is more accurate. The method of the embodiment of the present disclosure is particularly useful for instruments equipped without or not switching on an optical RET or optical PLT channel. Being independent of fluorescence detection, the instruments have reduced manufacturing costs and usage costs while maintaining high detection accuracy.

Figure 6:
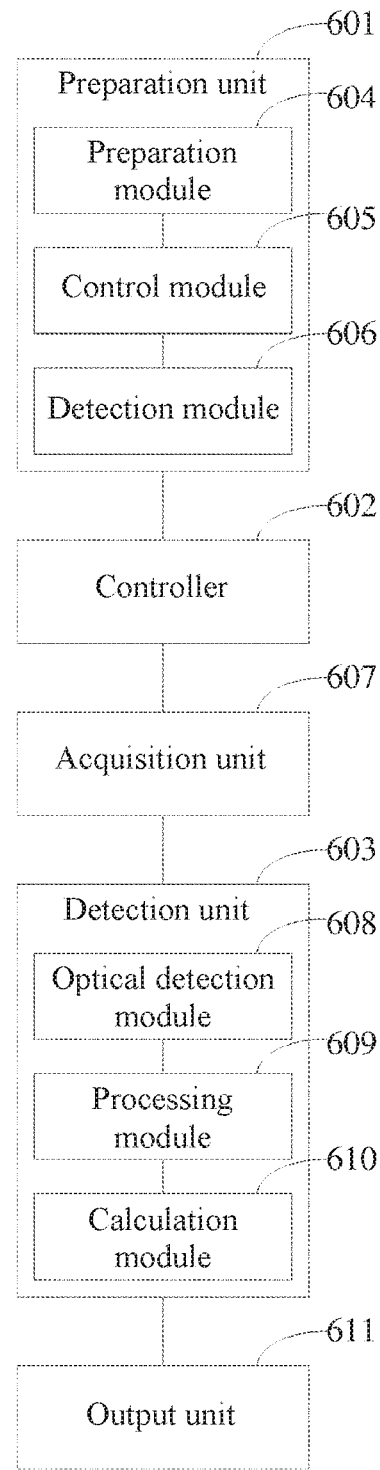
FIG. 6 is a schematic structure diagram of a blood testing apparatus provided by another embodiment of the present disclosure.

FIG. 6 is a schematic structure diagram of a blood testing apparatus provided by an embodiment of the present disclosure, which can be integrated in the blood testing apparatus shown in FIGS. 1 and 2 above, and the blood testing apparatus of the embodiment of the present disclosure can perform the blood testing method shown in scenario II above.

Referring to FIG. 6, the blood testing apparatus of the embodiment of the present disclosure includes a preparation unit 601 configured for preparing a second test solution by using the blood sample when low platelet count information of the blood sample is obtained, a controller 602 configured for controlling the second test solution to pass through an RET detection area, and a detection unit 603 configured for performing optical detection on the second test solution in the RET detection area to obtain an RET detection result and a second platelet detection result. The low platelet count information indicates that a platelet content of the blood sample is less than a preset platelet detection threshold. The statistical amount of the second test solution passing through the RET detection area is greater than a preset statistical amount.

Optionally, the preparation unit 601 further includes a preparation module 604 including a sampling part, a reaction part and a reagent supply part. The sampling part samples and conveys a blood sample to the reaction part, the reagent supply part supplies a reagent to the reaction part, and the blood sample and the reagent are prepared into a first test solution in the reaction part. The preparation unit 61 also includes a control module 605 configured for controlling the first test solution to pass through an impedance detection area, and a detection module 606 including a sample tube and an impedance detector. The sample tube conveys the first test solution through the impedance detector for platelet detection, and the detector collects signals and obtains a first platelet detection result according to the signals.

The preparation module 604 is further configured for preparing a second test solution by using the blood sample when the first platelet detection result is less than the preset platelet detection threshold.

Optionally, the detection unit 603 is further configured for performing optical detection on the second test solution in the RET detection area within a target time period to obtain an RET detection result and a second platelet detection result, the target time period being greater than a preset time period, and the preset time period corresponding to the preset statistical amount.

Optionally, the preparation unit 601 is further configured for preparing a second test solution by using the blood sample when the first platelet detection result is less than a preset platelet detection threshold and abnormal detection information of red blood cell of the blood sample is acquired.

Optionally, the blood testing apparatus of the embodiment of the present disclosure further includes an acquisition unit 607 configured for acquiring a platelet detection threshold input by a user.

The preparation unit 601 is further configured for preparing a second test solution by using the blood sample when the first platelet detection result is less than the platelet detection threshold.

Optionally, the detection unit 603 includes an optical detection module 608 configured for performing optical detection on the second test solution in the RET detection area, and a processing module 609 configured for collecting and storing a first light scatter signal and a first fluorescence signal of cells in the second test solution one by one within a first detection time period. The processing module 609 is further configured for collecting a second light scatter signal and a second fluorescence signal of cells in the second test solution one by one within a second detection time period, determining whether intensity of scattered light of the second light scatter signal is greater than or equal to a preset intensity threshold. The processing module 609 stops storing the second light scatter signal and the second fluorescence signal if the intensity of scattered light of the second light scatter signal is greater than or equal to the preset intensity threshold, or stores the second light scatter signal and the second fluorescence signal if the intensity of scattered light of the second light scatter signal is less than the preset intensity threshold.

Optionally, the detection unit 603 further includes a calculation module 610 configured for calculating an RET detection result according to the first light scatter signal and the first fluorescence signal stored within the first detection time period. The calculation module 610 is further configured for calculating a second platelet detection result according to the first light scatter signal and the first fluorescence signal stored within the first detection time period and the second light scatter signal and the second fluorescence signal stored within the second detection time period. Within the first detection time period and the second detection time period, the statistical amount of the second test solution passing through the RET detection area is greater than the preset statistical amount.

Optionally, the first light scatter signal and the second light scatter signal are forward scatter signals.

Optionally, within the first detection time period, the statistical amount of the second test solution passing through the RET detection area is a preset RET statistical amount.

Optionally, the blood testing apparatus of the embodiment of the present disclosure further comprises an output unit 611. The output unit 611 is configured for outputting the RET detection result and the second platelet detection result.

In summary, the preparation unit 601 prepares a second test solution by using the blood sample when low platelet count information of the blood sample is obtained. The low platelet count information indicates that a platelet content of the blood sample is less than a preset platelet detection threshold. The controller 602 controls the second test solution to pass through the RET detection area; and the detection unit 603 carries out optical detection on the second test solution in the RET detection area to obtain an RET detection result and a second platelet detection result. The statistical amount of the second test solution passing through the RET detection area is greater than a preset statistical amount. The apparatus of the embodiment of the present disclosure is an instrument equipped with and switching on an optical RET channel. When a blood sample acquired is a low platelet count sample, optical detection is carried out on platelets and RETs of the blood sample by using a test solution of an increased statistical amount in the RET detection area, which improves the accuracy of platelet detection as well as the detection efficiency, since the RET detection and PLT-O detection are completed at once to obtain the RET detection result and PLT detection result simultaneously, thus reducing the consumption of samples and reagents and lowering the costs.

In the above embodiments, the disclosure may be implemented in whole or in part by software, hardware, firmware, or any combination thereof. When implemented using software, it may be implemented in whole or in part in the form of a computer program product.

The computer program product comprises one or more computer instructions. When the instructions of the computer program are loaded and executed on a computer, the processes or functions according to the embodiments of the present disclosure are generated in whole or in part. The computer may be a general-purpose computer, a special-purpose computer, a computer network, or other programmable devices. The computer instructions may be stored in a computer-readable storage medium or transmitted from one computer-readable storage medium to another. For example, the computer instructions may be transmitted from one website, computer, server or data center to another website, computer, server or data center in a wired manner (e.g., by a coaxial cable, an optical fiber, or a digital subscriber line (DSL)) or a wireless manner (e.g., infrared, and microwave methods). The computer readable storage medium may be any available medium that a computer can store data with or a data storage device such as a server, a data center, or the like that comprises one or more integrated available media. The available medium may be a magnetic medium (e.g., floppy disk, hard disk, magnetic tape), an optical medium (e.g., DVD), or a semiconductor medium (e.g., solid state disk (SSD)), etc.

Those skilled in the art can clearly understand that for convenience and conciseness of description, the specific working processes of the above-described systems, devices and units can refer to the corresponding processes in the above-described embodiments of the method and will not be further described here.

In several embodiments provided in this application, it is to be understood that the disclosed systems, devices and methods may be implemented in other ways. For example, the apparatus embodiments described above are only for illustration. For example, the division of the units is only a logic function division. In actual implementation, there may be other division methods, for example, multiple units or assemblies may be combined or integrated into another system, or some features may be omitted or not implemented. In a further aspect, the mutual coupling or direct coupling or communication connection shown or discussed may be indirect coupling or communication connection through some interfaces, devices or units, and may be in electrical, mechanical or other forms.

The units described as separate parts may or may not be physically separated, and the parts displayed as units may or may not be physical units, i.e., may be located in one place or may be distributed over multiple network units. Some or all of the units can be selected according to actual needs to achieve the purpose of the present embodiment.

In addition, the functional units in the embodiments of the present disclosure may be integrated into one processing unit or may alternatively exist as being physically separate, or two or more of the units may be integrated into one unit. The above integrated unit can be implemented in the form of hardware or a software function unit.

If the integrated unit is implemented in the form of a software function unit and sold or used as an independent product, it may be stored in a computer readable storage medium. Based on such understanding, the essence or, in other words, the part that contributes to the prior art of the technical solution of the present disclosure or all or part of the technical solution can be embodied in the form of a software product, which is stored in a storage medium and comprises a number of instructions to cause a computer device (which can be a personal computer, a server, or a network device, etc.) to perform all or part of the steps of the method described in various embodiments of the present disclosure. The aforementioned storage medium includes: a U disk, a removable hard disk, read-only memory (ROM), a random access memory (RAM), a magnetic disk or an optical disk and other media that can store program codes.

As described above, the above embodiments are only for the purpose of illustration of the technical solution of the present disclosure and not limitation. Although the present disclosure has been described in detail with reference to the foregoing embodiments, it should be understood by those of ordinary skill in the art that modifications can still be made to the technical solution described in the foregoing embodiments or equivalent substitutions of some technical features thereof is also possible, while these modifications or substitutions do not make the essence of the corresponding technical solution depart from the spirit and scope of the technical solutions of the embodiments of the present disclosure.

What is claimed is:

1. A blood testing method, comprising:
preparing a first test solution by using a blood sample;
controlling a first portion of the first test solution to pass through an impedance detection area, and controlling platelets in the first portion of the first test solution to pass through the impedance detection area one by one;
detecting the platelets of the first portion of the first test solution by using an impedance method in the impedance detection area to obtain a first platelet count;
in response to determining that the first platelet count is less than a preset threshold, determining that a platelet content in the blood sample is a low platelet count, and preparing a second test solution by using the blood sample or by aspirating a remaining second portion of the first test solution;
controlling the second test solution to pass through the impedance detection area, and controlling platelets in the second test solution to pass through the impedance detection area one by one; and
detecting the platelets of the second test solution by using the impedance method in the impedance detection area to obtain a second platelet count, a volume of the second test solution for counting statistics being greater than a volume of the first portion of the first test solution for counting statistics.

2. The method of claim 1, wherein detecting the platelets of the first portion of the first test solution by using an impedance method in the impedance detection area comprises:
detecting the platelets of the first portion of the first test solution by using the impedance method in the impedance detection area within a first time period, and
detecting the platelets of the second test solution by using the impedance method in the impedance detection area comprises:
detecting the platelets of the second test solution by using the impedance method in the impedance detection area within a second time period, the second time period being greater than the first time period.

3. The method of claim 1, wherein in response to determining that the first platelet count is less than a preset threshold, preparing the second test solution by using the blood sample or by aspirating the remaining second portion of the first test solution comprises:
in response to determining that the first platelet count is less than the preset threshold and no abnormal detection information of red blood cell of the blood sample being acquired, preparing the second test solution by using the blood sample or by aspirating the remaining second portion of the first test solution; and
the method further comprises:
in response to determining that the first platelet count is less than the preset threshold and abnormal detection information of red blood cell of the blood sample being acquired, preparing a third test solution by using the blood sample;
controlling the third test solution to pass through an RET detection area; and
performing an optical detection on the third test solution in the RET detection area to obtain an RET detection result and a third platelet count, wherein a statistical amount of the third test solution passing through the RET detection area is greater than a predetermined statistical amount.

4. The method of claim 3, wherein performing the optical detection on the third test solution in the RET detection area to obtain the RET detection result and the third platelet count comprises:
illuminating the third test solution in the RET detection area by a light source;
collecting and storing a first light scatter signal and a first fluorescence signal of cells in the third test solution one by one within a first detection time period;
collecting a second light scatter signal and a second fluorescence signal of cells in the third test solution one by one within a second detection time period; only if a light intensity of the second light scatter signal is less than a predetermined intensity threshold, storing the second light scatter signal and the second fluorescence signal;
calculating the RET detection result according to the first light scatter signal and the first fluorescence signal stored during the first detection time period; and
calculating the third platelet count according to the first light scatter signal and the first fluorescence signal stored during the first detection time period and the second light scatter signal and the second fluorescence signal stored during the second detection time period.

5. The method of claim 4, wherein the first light scatter signal and the second light scatter signal are forward scatter signals.

6. The method of claim 1, further comprising:
in response to determining that the first platelet count is less than the preset threshold and no abnormal detection information of red blood cell of the blood sample being acquired, re-measuring the platelets of the blood sample by using the impedance method; and
in response to determining that the first platelet count is less than the preset threshold and abnormal detection information of red blood cell of the blood sample being acquired, re-measuring the platelets of the blood sample by using an optical detection method.

7. A blood testing method, comprising:
preparing a first test solution by using a blood sample;
controlling a first statistical amount of the first test solution to pass through an impedance detection area, and controlling platelets in the first test solution to pass through the impedance detection area one by one;
detecting the platelets in the first statistical amount of the first test solution by using an impedance method in the impedance detection area to obtain a first platelet count;
in response to determining that the first platelet count is less than a preset threshold, determining that a platelet content in the blood sample is a low platelet count, and preparing a second test solution by using the blood sample or by aspirating a remaining test solution of the first test solution, wherein the preset threshold is a threshold for determining whether the platelet content in the blood sample is the low platelet count;
controlling a second statistical amount of the second test solution to pass through the impedance detection area, and controlling platelets in the second test solution to pass through the impedance detection area one by one; and
detecting the platelets in the second statistical amount of the second test solution by using the impedance method in the impedance detection area to obtain a second platelet count, a volume of the second test solution for counting statistics being greater than a volume of the first test solution for counting statistics.

* * * * *